United States Patent
Mikajiri (10) Patent No.: US 10,426,431 B2
(45) Date of Patent: Oct. 1, 2019

(54) PROTECTION CIRCUIT

(71) Applicant: CANON KABUSHIKI KAISHA, Tokyo (JP)

(72) Inventor: Satoru Mikajiri, Tokyo (JP)

(73) Assignee: Canon Kabushiki Kaisha, Tokyo (JP)

( * ) Notice: Subject to any disclaimer, the term of this patent is extended or adjusted under 35 U.S.C. 154(b) by 961 days.

(21) Appl. No.: 14/939,448

(22) Filed: Nov. 12, 2015

(65) Prior Publication Data

US 2016/0141864 A1    May 19, 2016

(30) Foreign Application Priority Data

Nov. 19, 2014 (JP) .................. 2014-234525

(51) Int. Cl.

| | | |
|---|---|---|
| H03K 17/687 | (2006.01) | |
| A61B 8/14 | (2006.01) | |
| H01L 27/02 | (2006.01) | |
| A61B 8/00 | (2006.01) | |
| B06B 1/02 | (2006.01) | |
| H03F 1/52 | (2006.01) | |
| H02H 9/04 | (2006.01) | |

(52) U.S. Cl.

CPC .................. *A61B 8/14* (2013.01); *A61B 8/56* (2013.01); *B06B 1/0207* (2013.01); *H01L 27/0266* (2013.01); *H03F 1/523* (2013.01); *A61B 8/4483* (2013.01); *H02H 9/046* (2013.01)

(58) Field of Classification Search
None
See application file for complete search history.

(56) References Cited

U.S. PATENT DOCUMENTS

| | | | | |
|---|---|---|---|---|
| 5,736,877 A | * | 4/1998 | Tihanyi | H02H 3/12 327/109 |
| 8,222,928 B2 | * | 7/2012 | Bayerer | H03K 17/567 327/108 |
| 9,118,180 B2 | * | 8/2015 | Yasuda | H02H 3/207 |
| 9,564,828 B2 | * | 2/2017 | Siessegger | H05B 33/0806 |
| 2013/0229740 A1 | | 9/2013 | Yasuda et al. | |
| 2014/0070319 A1 | * | 3/2014 | Tonomura | H01L 27/0211 257/355 |
| 2014/0091384 A1 | * | 4/2014 | Petruzzi | H01L 27/0922 257/329 |

(Continued)

FOREIGN PATENT DOCUMENTS

| | | |
|---|---|---|
| JP | 5-48021 A | 2/1993 |
| JP | 2012-10831 A | 1/2012 |
| JP | 2013-211522 A | 10/2013 |

OTHER PUBLICATIONS

Office Action in Japanese Patent Application No. 2014-234525, dated Jun. 12, 2018.

(Continued)

*Primary Examiner* — Lincoln D Donovan
*Assistant Examiner* — Khareem E Almo
(74) *Attorney, Agent, or Firm* — Venable LLP (57) ABSTRACT

A P-channel type MOSFET and an N-channel type MOSFET formed by a CMOS process are connected in series. A high-voltage signal and a low-voltage signal are applied to the drain of one of transistors. Prescribed bias voltage is applied to both gates in order that only a low-voltage signal can pass through both conduction paths.

14 Claims, 9 Drawing Sheets

(56) References Cited

U.S. PATENT DOCUMENTS

| | | | | |
|---|---|---|---|---|
| 2015/0057539 A1* | 2/2015 | Thorsen | ................... | H03K 3/57 |
| | | | | 600/437 |
| 2015/0091641 A1* | 4/2015 | Mauder | ................... | H01L 29/78 |
| | | | | 327/566 |
| 2016/0087579 A1* | 3/2016 | Moslehi | .............. | H01L 31/0516 |
| | | | | 136/251 |
| 2016/0141864 A1* | 5/2016 | Mikajiri | ................. | H03F 1/523 |
| | | | | 600/437 |
| 2018/0013415 A1* | 1/2018 | Ikeda | ..................... | H03K 17/74 |
| 2018/0109251 A1* | 4/2018 | Djelassi | ........... | H03K 3/356182 |

OTHER PUBLICATIONS

English translation of Jun. 12, 2018 Office Action in Japanese Patent Application No. 2014-234525.

* cited by examiner

PROTECTION CIRCUIT

BACKGROUND OF THE INVENTION

Field of the Invention

The present invention relates to a protection circuit.

Description of the Related Art

An ultrasound transducer in an ultrasound diagnostic apparatus sends ultrasound waves on the basis of positive and negative high-voltage signals, and outputs a low-voltage signal obtained by receiving these very slight ultrasound waves, to a reception circuit. Therefore, a protection circuit which protects the amplifier circuit that amplifies the low-voltage signals output from the ultrasound transducer, against the high-voltage signals of both negative and positive polarity used to drive the ultrasound transducer, is required between the ultrasound transducer and the reception circuit which send and receive ultrasound waves. When a high-voltage signal is applied, this protection circuit switches off and thereby shuts off the high-voltage signal. Furthermore, when a low-voltage signal is applied, the circuit switches on to enable the low-voltage signal to pass to the reception circuit. For example, whereas a high-voltage signal has a voltage of approximately several ten to several hundred V, of negative or positive polarity, the amplification circuit is composed by devices capable of withstanding a voltage of approximately 5 V.

The number of channels in the transducer of an ultrasound diagnostic apparatus is large (several hundred channels), and the signal transmission/reception circuit is required to have a corresponding number of channels. Moreover, the timings at which transmission pulses are sent in each channel are variable. On the other hand, if the protection circuit is switched on and off using a control signal, then it is necessary to implement continuous control so as to pass low-voltage signals when the circuit is on and to shut off high-voltage signals when the circuit is off, and a number of signal lines corresponding to the number of channels are required and hence costs increase. Therefore, it is necessary to provide a protection circuit having a function for passing low-voltage signals and shutting out high-voltage signals, without the need for an external control signal.

In the prior art, a circuit provided with a circuit for detecting a high-voltage signal, or a circuit employing a depletion-mode FET, has been used in order to achieve a protection circuit that operates without a control signal (see Japanese Patent Application Publication No. 2012-10831 and Japanese Patent Application Publication No. H5-48021).

SUMMARY OF THE INVENTION

The problems in achieving a protection circuit which operates without an external control signal can be divided broadly into two. Firstly, there is the problem of increase in the scale of the circuitry. For example, in the apparatus disclosed in Japanese Patent Application Publication No. 2012-10831, a circuit which detects a high-voltage signal is used. When a circuit for switching a protection circuit on and off is achieved by detecting high-voltage signals in this way, then it is necessary to provide a circuit for detecting the high-voltage signals and a drive circuit for operating the protection circuit in accordance with the detection results.

In this case, the detection unit needs to have a high voltage resistance, and there is a problem in that since the drive circuit for operating the protection circuit is also necessary when configuring the protection circuit, then the circuitry becomes complicated.

Secondly, special processes, such as depletion-mode FET, become necessary. When the protection circuit described above is achieved by a circuit having a reduced number of elements which does not employ a detection circuit, then a normally-on depletion-mode FET is used. However, this FET is problematic in that it requires special processing and costs increase.

In view of the foregoing, it is an object of the present invention to provide a protection circuit capable of passing a low-voltage signal as well as protecting internal circuitry which has low voltage resistance, from high voltages of both polarities, with a small circuit size and without requiring special processes.

The present invention in its one aspect provides a protection circuit, comprises a first enhancement-type MOS transistor of a first conductivity type having a drain, a source and a gate; a second enhancement-type MOS transistor of a second conductivity type having a drain connected to the source of the first enhancement-type MOS transistor, a source, and a gate to which a first bias voltage is supplied; a diode element having one end connected to the drain of the first enhancement-type MOS transistor, and another end connected to the gate of the first enhancement-type MOS transistor; and a current source having one end connected to the gate of the first enhancement-type MOS transistor and the other end of the diode element, and another end to which a second bias voltage is supplied.

The present invention in its another aspect provides a protection circuit, comprises a first enhancement-type MOS transistor of a first conductivity type having a drain, a source and a gate; a second enhancement-type MOS transistor of a second conductivity type having a drain connected to the source of the first enhancement-type MOS transistor, a source, and a gate to which a first bias voltage is supplied; a diode element having one end connected to the source of the first enhancement-type MOS transistor, and another end connected to the gate of the first enhancement-type MOS transistor; and a current source having one end connected to the gate of the first enhancement-type MOS transistor and the other end of the diode element, and another end to which a second bias voltage is supplied.

The present invention in its another aspect provides a protection circuit, comprises a first enhancement-type MOS transistor of a first conductivity type having a drain, a source and a gate; a second enhancement-type MOS transistor of a second conductivity type having a drain connected to the source of the first enhancement-type MOS transistor, a source, and a gate to which a first bias voltage is supplied; a diode element having one end connected to the drain of the first enhancement-type MOS transistor, and another end connected to the gate of the first enhancement-type MOS transistor; and a resistance having one end connected to the gate of the first enhancement-type MOS transistor and the other end of the diode element, and another end to which a second bias voltage is supplied.

According to the present invention, it is possible to provide a protection circuit capable of passing a low-voltage signal as well as protecting internal circuitry which has low voltage resistance, from high voltages of both polarities, with a small circuit size and without requiring special processes.

Further features of the present invention will become apparent from the following description of exemplary embodiments with reference to the attached drawings.

DESCRIPTION OF THE EMBODIMENTS

Embodiments of the present invention are described in detail below with reference to the drawings. In principle, the same constituent elements are labelled with the same reference numerals and description thereof is omitted. The detailed calculation formula and calculation procedure, and the like, described below should be changed appropriately depending on the composition and various conditions of the apparatus to which the invention is applied, and it is not intended to limit the scope of the invention to the description of the embodiments given below.

The ultrasound diagnostic apparatus having the protection circuit of the present invention includes an apparatus which uses ultrasound echo technology in which an ultrasound wave is transmitted to the object, a reflected wave (echo wave) reflected inside the object is received, and object information is acquired as image data. Furthermore, this ultrasound diagnostic apparatus includes one which combines use of an apparatus employing a photoacoustic effect in which an ultrasound wave generated inside an object due to irradiating light (an electromagnetic wave) onto the object is received and object information is obtained as image data.

In the case of an ultrasound diagnostic apparatus, which is an apparatus using ultrasound echo technology, the acquired object information is information that reflects differences in the acoustic impedance of the tissue inside the object. The object information acquired by an apparatus using a photoacoustic effect indicates the distribution of a generation source of an acoustic wave which is generated by the irradiation of light, the initial sound pressure distribution inside the object, or a light energy absorption density distribution or absorption coefficient distribution derived from the initial sound pressure distribution, and the density distribution of the material constituting tissue. The density distribution of the material is, for instance, the oxygen saturation distribution, or oxidized/reduced hemoglobin density distribution, etc.

The acoustic wave referred to in the present invention is typically an ultrasound wave, and includes elastic waves called sound waves, ultrasound waves or acoustic waves.

First Embodiment

Figure 1:
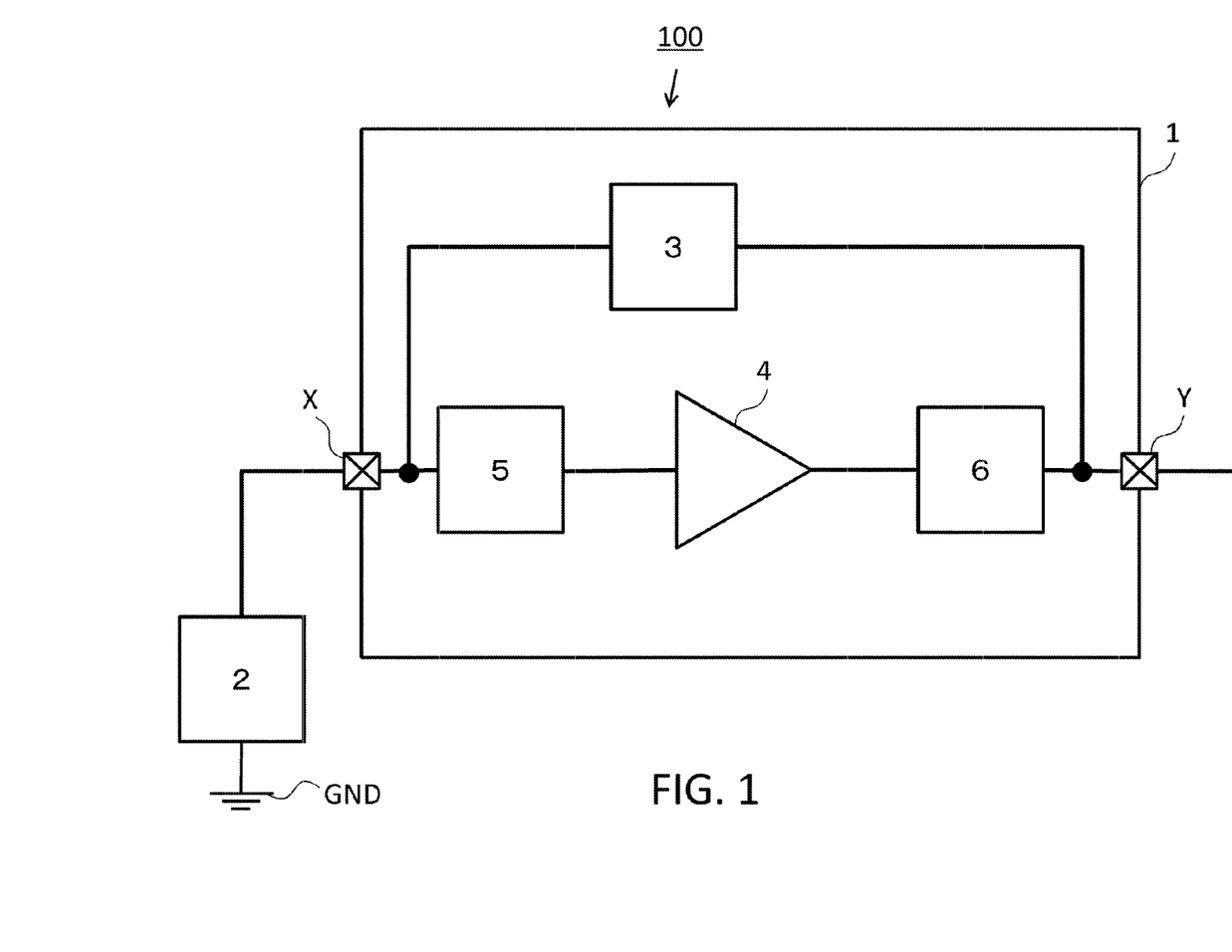
FIG. 1 is a block diagram showing a first embodiment of a protection circuit according to the present invention.

FIG. 1 is a block diagram showing a first embodiment of a protection circuit according to the present invention. The ultrasound diagnostic apparatus 100 (called "apparatus 100" below), which is an object information acquisition apparatus of the present embodiment, has a basic configuration of an ultrasound wave transmission and reception circuit 1 (abbreviated as "transmission and reception circuit 1" below) and an ultrasound wave transducer 2 (abbreviated as "element 2" below). The transmission and reception circuit 1 has a transmission circuit 3, a low-voltage amplification circuit 4, an input protection circuit 5 and an output protection circuit 6. The ultrasound wave transmission and reception circuit 1 is provided with external terminals X and Y, and signals are transmitted to and received from external apparatuses via the external terminals X and Y.

The transmission and reception circuit 1 refers to the whole circuit block of the ultrasound wave diagnostic apparatus. The element 2 is an element which receives a high-voltage signal from the transmission and reception circuit 1, transmits an ultrasound wave to an object, receives an ultrasound wave reflected from the object, and outputs a low-voltage signal. The transmission circuit 3 is a circuit provided in the signal transmission path when transmitting a high-voltage signal to the element 2. The low-voltage amplification circuit 4 amplifies the low-voltage signal (reception signal) output from the element 2 upon receiving an ultrasound wave from the object. The input protection circuit 5 and the output protection circuit 6 are circuits which respectively protect the input and the output of the low-voltage amplification circuit 4, from high-voltage signals. The low-voltage signal is a signal having a smaller voltage amplitude than the high-voltage signal.

The transmission and reception circuit 1 is connected to the element 2, which transmits and receives ultrasound signals, via the external terminal X. The transmission and reception circuit 1 supplies a high-voltage signal having a voltage amplitude from approximately several ten to several hundred V, for instance, (here, for example, a high-voltage signal of $>-100V$ and $<-10V$ or a high-voltage signal of $>+10V$ and $<+100V$) to the element 2. The element 2 outputs a low-voltage signal having a voltage amplitude of no more than several V (here, for example, a low-voltage signal of $>-1V$ and $<+1V$), for example, as the reception signal. In the low-voltage amplification circuit 4, the voltage resistance is designed to be approximately 5V. These high-voltage and low-voltage signals are applied to the external terminals X and Y. Therefore, in the low-voltage amplification circuit 4, an input-side and an output-side protection circuit 5 and 6 are provided respectively in order to prevent infiltration of high-voltage signals which exceed the voltage resistance. Furthermore, in the protection circuits 5 and 6, it is necessary for the signal to pass from the external terminal X to the external terminal Y when a low-voltage signal is applied, in order to input a low-voltage signal to the low-voltage amplification circuit 4 and to output an amplified signal. The apparatus 100 of the present embodiment has protection circuits 5 and 6 which have a function for shutting off high-voltage signals and passing low-voltage signals.

Figure 2A:
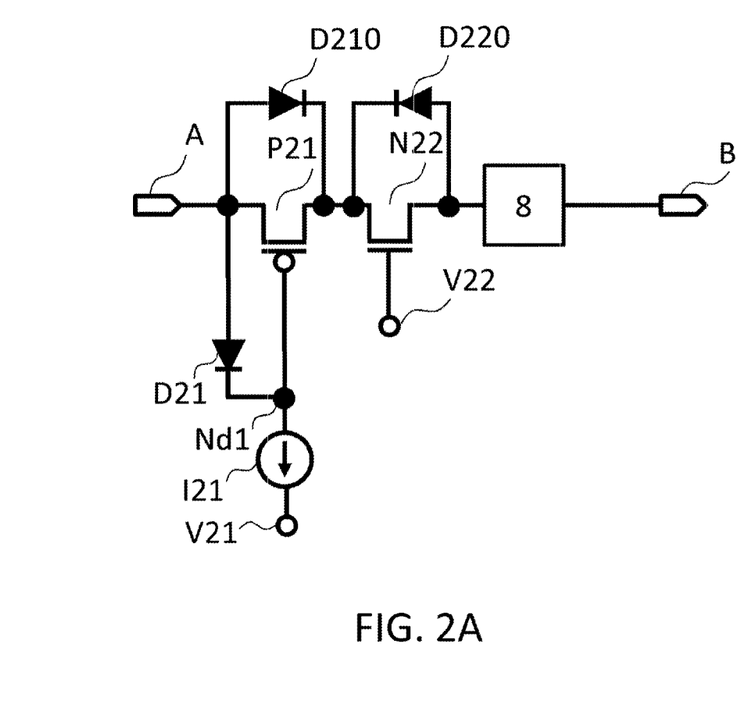
FIGS. 2A and 2B are diagrams showing the configuration of a protection circuit according to the first embodiment.
Figure 2B:
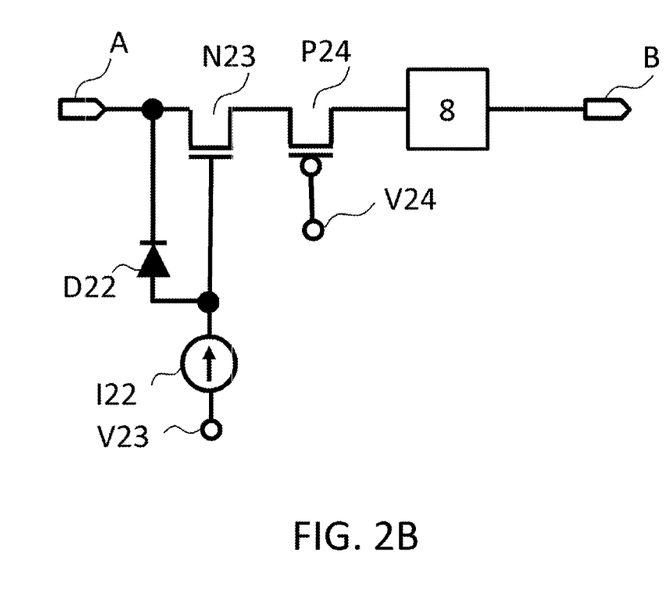

FIG. 2A and FIG. 2B are diagrams showing the circuit configuration of protection circuits in the first embodiment, and constituent elements which are the same as FIG. 1 are labelled with the same reference numerals and description thereof is omitted apart from particular circumstances. FIG. 2A shows the basic circuit configuration of the protection circuits 5 and 6. The protection circuits 5 and 6 have the same configuration and therefore only the protection circuit 5 is described apart from particular circumstances. The protection circuit 5 includes an enhancement-type P-channel MOSFET (Field Effect Transistor) (corresponding to an enhancement-type MOS transistor of a first or second conduction type, and an enhancement-type P-channel MOS transistor; P21 (abbreviated as "transistor P21") below). Moreover, the protection circuit 5 includes an enhancement-type N-channel MOSFET (corresponding to an enhancement-type MOS transistor of a first or second conduction type, and an enhancement-type N-channel MOS transistor; N22 (abbreviated as "transistor N22") below). Moreover, the protection circuit 5 includes a diode D21 (which has a threshold voltage of 0.6V, for example), a current source I21 and a voltage limiting circuit 8. Furthermore, the protection circuit 5 has a terminal to which a constant voltage V21 is applied (for example, approximately several minus V, taken here to be −3V), and a terminal to which a constant voltage V22 is applied (for example, approximately several plus V, taken here to be +3V), and terminals A and B. When the low-voltage signal does not have a negative value, for example, when the central value of the voltage amplitude is +1V and oscillates by approximately ±1V, then the constant voltage V21 may be a positive voltage.

The terminal A is a terminal to which a high-voltage signal is applied, and the terminal B is a terminal to which the low-voltage circuit is connected. To give an example of the connection of the terminals A and B, when applied to the protection circuit 5 of the block in FIG. 1, the terminal A is connected to the element 2, of which one end is connected via the external terminal X to ground GND, which is a reference voltage, and terminal B is connected to the input terminal of the low-voltage amplification circuit 4. When applied to the protection circuit 6, the terminal B is connected to the output terminal of the low-voltage amplification circuit 4, and the terminal A is connected to the external terminal Y which is on the side to which the high-voltage signal is input. In the present embodiment, ground GND (0V) is employed as the reference voltage, but the reference voltage is not limited to this and the value of the reference voltage may be changed as appropriate. For example, when a positive reference voltage is employed as the reference voltage, then the high-voltage signal oscillates in the positive direction and the negative direction about this reference voltage, but whichever way the signal oscillates, a positive voltage value can be obtained. This also applies to the case of the low-voltage signal.

When a positive or negative high-voltage is applied, the voltage limiting circuit 8 clamps the voltage value to a prescribed value, and this circuit 8 is an electrostatic discharge protection circuit (ESD), for example, which is connected between the source and terminal B of the transistor N22. However, the invention is not limited to this, and the voltage limiting circuit 8 may be incorporated into the low-voltage amplification circuit 4.

The basic configuration of the protection circuit shown in FIG. 2A is formed by a parallel connection of enhancement-mode P and N-channel MOS transistors which are formed by a CMOS process. More specifically, the terminal A is connected to the drain of the transistor P21. The terminal B is connected to the source of the transistor N22 via the voltage limiting circuit 8. Furthermore, a source of the transistor P21 and the drain of the transistor N22 are connected. A constant voltage V22 is supplied to the gate of the transistor N22. One end of the constant current source I21 is connected to the gate of the transistor P21, and the constant voltage V21 is supplied to the other end of the current source I21. The constant current source I21 is connected in a direction whereby the current is drawn in from the source Nd1. The constant current source I21 may be configured by a current mirror circuit, or the like, or may be configured by another circuit.

The anode of the gate protection diode D21 is connected to the drain of the transistor P21 and the cathode thereof is connected to the gate of the transistor P21. The forward-direction threshold value VD21 of the gate protection diode D21 is set so as to exceed the threshold value VP21 of the transistor P21 (|VD21|>|VP21|). Furthermore, the drain-source voltage resistance of the transistor P21 and the transistor N22 must be greater than the absolute value of the voltage of the high-voltage signal. The absolute value of the low-voltage signal is a value equal to or lower than the voltage resistance of the circuit connected to terminal B of the protection circuit 5. The voltage limiting circuit 8 limits the absolute value of the low-voltage signal to no more than the voltage resistance of the low-voltage amplification circuit 4 (corresponding to the external circuit), which is a circuit in which the absolute value of the low-voltage signal is connected to the terminal B. In the present embodiment, the gate protection diode D21 uses the parasitic diode of transistor P21. However, the invention is not limited to this, and a diode element may also be connected between the drain and gate, separately from the transistor P21, or a transistor connected to the diode may be used. Furthermore, it is also possible to use a Zener diode and/or Schottky diode.

Next, the operation of the protection circuit described above will be explained on the basis of FIG. 2A. Firstly, when a low-voltage signal is applied to terminal A, voltages exceeding the respective threshold values VP21, VN22 are applied to the respective gates of the transistor P21 and the transistor N22. In other words, constant voltages V21, V22 sufficient to switch on the transistor P21 and transistor N22 are applied to the gates. In so doing, the transistor P21 and the transistor N22 switch on and pass a low-voltage signal.

Next, the operation of the protection circuit 5 when a high-voltage signal is applied to the terminal A will be described.

When a positive high-voltage signal is applied to the terminal A, then a high voltage is applied to the drain of the transistor P21. In this case, a parasitic diode D210 is present between the drain and source of the transistor P21 and this parasitic diode D210 switches on. In other words, the transistor P21 allows the high-voltage signal applied to the drain of the transistor P21, to pass to the source side thereof, via the parasitic diode D210 therein. In this case, the diode D21 is switched on. Consequently, the voltage occurring at the gate of the transistor P21 is lower than the drain voltage of the transistor P21 by an amount corresponding to the forward-direction voltage drop VD21 of the diode D21. In this way, the diode D21 limits the gate-source voltage of the transistor P21 to the threshold value of the diode D21, thereby preventing the voltage from exceeding the voltage resistance, and suppresses gate breakdown in the transistor P21. Furthermore, in this case, the current source I21 limits the current flowing the diode D21 to the set current value.

Next, a high-voltage signal passing through the parasitic diode 210 of the transistor P21 is applied to the drain of the transistor N22. Immediately after the positive high-voltage signal has been applied to the terminal A, the transistor N22 remains in a switched on state. Therefore, the source voltage of the transistor N22 also increases simultaneously with the appearance of the positive high-voltage signal at the drain of the transistor N22. In this case, the source voltage of the transistor N22 increases until reaching the voltage set by the voltage limiting circuit 8 which is connected to the terminal B. When the source voltage of the transistor N22 exceeds the bias voltage V22 at the gate of the transistor N22 minus the threshold value VN22 of the transistor N22, then the transistor N22 operates as a clip circuit. Consequently, a limit is applied to the voltage when the source voltage of the transistor N22 has reached a voltage equal to or greater than the bias voltage V22 at the gate of the transistor N22 minus the threshold value VN22 of the transistor N22.

Next, when a negative high voltage is applied to the terminal A, the drain voltage of the transistor P21 falls to a negative high voltage which is equal to or less than ground (GND). In this case, in the gate protection diode D21, the breakdown voltage of the diode is set to be sufficiently greater than the voltage present at the cathode of the diode minus the voltage present at the anode of the diode. Therefore, the diode D21 does not produce an avalanche breakdown, even when a high voltage is applied in the reverse direction, and does not pass current in the reverse direction or the forward direction. Therefore, a constant voltage V21 connected to one end of the current source I21 is present at the gate of the transistor P21. On this basis, if the source voltage of the transistor P21 when the transistor is on is lower than the gate voltage of the transistor plus the threshold value of the transistor, then the transistor P21 switches off. Furthermore, the source voltage of the transistor P21 is limited by the voltage that is limited by the voltage limiting circuit 8 connected to the terminal B and the threshold value of the parasitic diode D220 between the drain and source of the transistor N22.

By means of the operations described above, a protection circuit which protects the low-voltage amplification circuit (corresponding to an amplifier) from high-voltage signals of positive and negative polarity, without requiring a control signal, and which also passes small signals, can be achieved. In the present embodiment, a low-voltage amplification circuit was used, but the invention is not limited to this and it is also possible to use the protection circuit of the present embodiment to protect other circuits having a low voltage resistance.

FIG. 2B is a circuit configuration in which the polarities are different from the protection circuit illustrated in FIG. 2A of the first embodiment. More specifically, in this circuit, the transistors P21, N22 in FIG. 2A are replaced respectively by an enhancement-type N-channel MOS transistor N23 and an enhancement-type P-channel MOS transistor P24, as shown in FIG. 2B. In this case, the orientation of the current source I22 and the orientation of the protection diode D22 are reversed, whereby the same functions as the protection circuit in FIG. 2A can be achieved. In this case also, the threshold value in the forward direction of the protection diode D22 is set so as to exceed the absolute value of the threshold value of the enhancement-type N-channel MOS transistor N23. This protection diode D22 also uses the parasitic diode of the enhancement-type N-channel MOS transistor N23, but similarly to the foregoing, is not limited to this and may employ various diode elements. The constant voltages V23, V24 are respectively, +3V and −3V, for example. The threshold value in the forward direction of the diode D22 is 0.6 V, for example.

Figure 3:
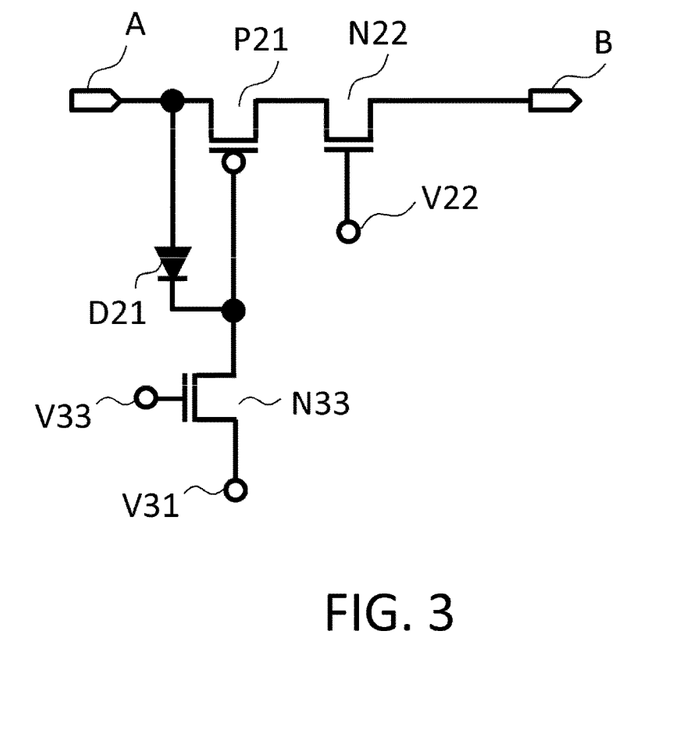
FIG. 3 is a diagram showing one example of a current source according to the first embodiment.

FIG. 3 is a diagram showing one example of a current source in the first embodiment, and constituent elements which are the same as FIG. 1 are labelled with the same reference numerals and description thereof is omitted apart from particular circumstances. In FIG. 3, the current source I21 is configured by an enhancement-type N-channel MOSFET N33 (abbreviated to "transistor N33" below). A constant voltage V31 is supplied to the source of the transistor N33, and a constant voltage V33 is connected to the gate of the transistor N33. The constant current source I21 which is configured in this way limits the current flowing between the drain and source of the transistor N33, and operates as a current source. In this case, the drain-gate and drain-source voltage resistances of the transistor N33 are set to a level sufficient to withstand the high-voltage signals applied to the terminal A. Furthermore, when the orientation of the current source is reversed with respect to I21, as shown in FIG. 2B, then this can be achieved by replacing the transistor N33 with an enhancement-type P-channel MOSFET.

Figure 4:
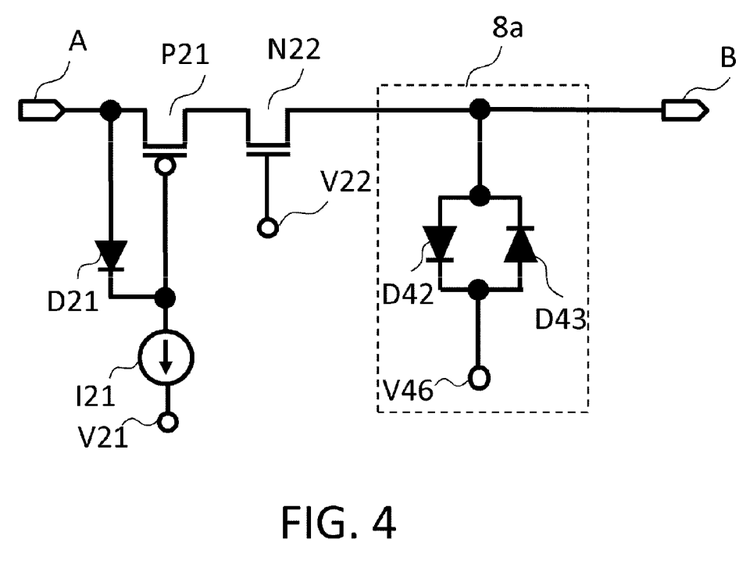
FIG. 4 is a diagram showing one example of a voltage limiting circuit according to the first embodiment.

FIG. 4 is a diagram showing one example of a voltage limiting circuit in the first embodiment, and constituent elements which are the same as FIG. 1 are labelled with the same reference numerals and description thereof is omitted apart from particular circumstances. In the voltage limiting circuit 8a in FIG. 4, the anode of the diode D42, the cathode of the diode D43 and the terminal B are connected commonly. Moreover, in the voltage limiting circuit 8a, the cathode of the diode D42, the anode of the diode D43 and the application terminal of the constant voltage V46 are connected commonly. The voltage limiting circuit 8a is a clip circuit which is configured as described above. By means of the diodes D42, D43, the voltage limiting circuit 8a limits the voltage V1 present at the terminal B to a range of (constant voltage V46+threshold value of diode D42<voltage V1<constant voltage V46−threshold value of diode D43). When the voltage limiting circuit 8a is connected to the protection circuit as in FIG. 4, then the gate voltage V22 of the transistor N22 must be set to a voltage equal to or greater than the sum of the constant voltage V46, the threshold voltage of the diode D42 and the threshold voltage of the transistor N22 (|constant voltage V22|>|constant voltage V46+threshold value of diode D42|+|threshold value of transistor N22|). The threshold values of the diode D42 and the diode D43 are substantially the same.

Figure 5:
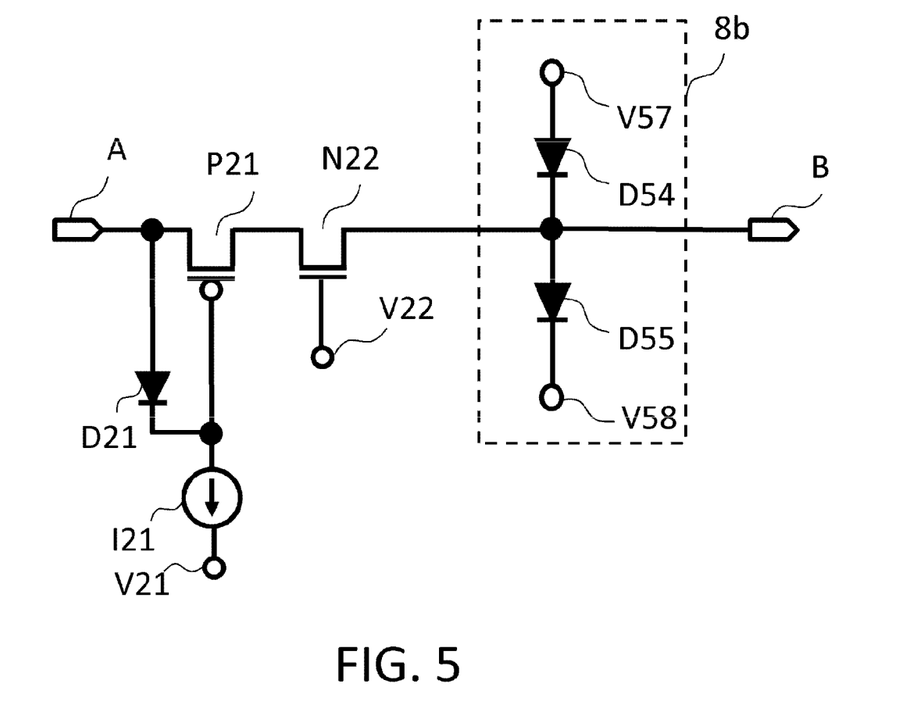
FIG. 5 is a diagram showing a further example of a voltage limiting circuit according to the first embodiment.

FIG. 5 is a diagram showing a further example of a voltage limiting circuit in the first embodiment, and constituent elements which are the same as FIG. 1 are labelled with the same reference numerals and description thereof is omitted apart from particular circumstances. In the voltage limiting circuit 8b (which corresponds to the clamp circuit), the cathode of the diode D54, the anode of the diode D55 and the terminal B are connected commonly. Moreover, in the voltage limiting circuit 8b, a constant voltage V57 is supplied to the anode of the diode D54 and a constant voltage V58 is supplied to the cathode of the diode D55. Consequently, in the voltage limiting circuit 8b, it is possible to limit the voltage V2 at the terminal B to a range of (constant voltage V57+threshold value of diode D54<V2<constant voltage V58+threshold value of diode D55). When the voltage limiting circuit 8b is connected to the circuit of FIG. 2A, as in FIG. 5, then the gate voltage V22 of the transistor N22 must be set to a voltage equal to or greater than the sum of the constant voltage V58, the threshold voltage of the diode D55 and the threshold voltage of the transistor N22 (|constant voltage V22|>|constant voltage V58+threshold value of diode D55|+|threshold value of transistor N22|). The threshold values of the diode D55 and the diode D54 are substantially the same.

Figure 6:
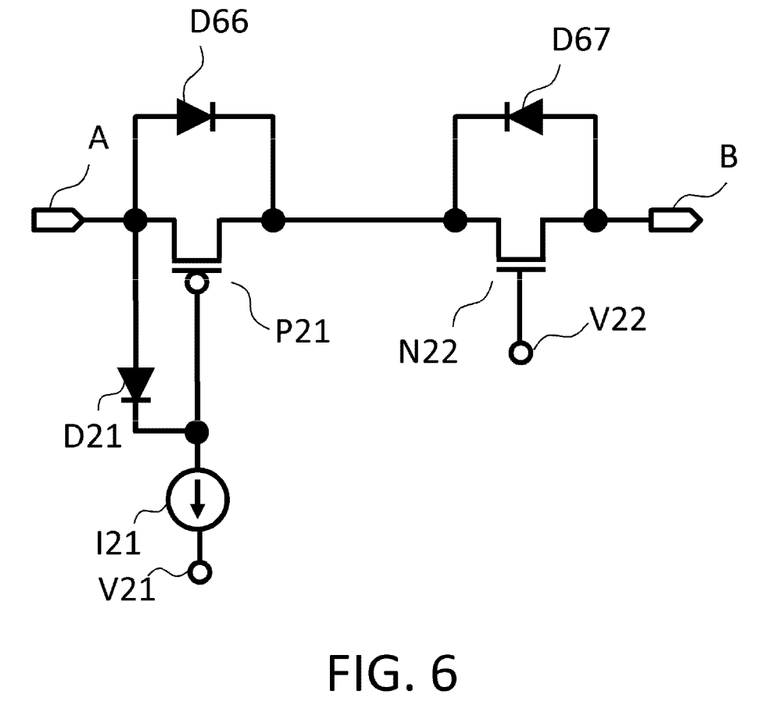
FIG. 6 is a diagram showing a further example of a protection circuit according to the first embodiment.

FIG. 6 is a diagram showing a further example of a protection circuit in the first embodiment, and constituent elements which are the same as FIG. 1 are labelled with the same reference numerals and description thereof is omitted apart from particular circumstances. The protection circuit in FIG. 6 is a circuit in which diodes D66, D67 bypassing the drain-source are respectively connected between the drain and source of the transistor P21 and the transistor N22 of the circuit in FIG. 2A. Consequently, it is possible to prevent an unexpected current from flowing in the parasitic diode which exists between the drain and source of the transistors P21 and N22. In other words, the respective threshold values of the diodes D66 and D67 are lower than the respective threshold values of the parasitic diodes in the transistors P21 and N22. By adopting a configuration of this kind, it is possible to prevent breakdown due to overcurrent in the transistors P21, N22 by bypassing the large current by the diodes D66, D67, when an unexpected large current is supplied to the transistors P21, N22. In this case, the breakdown voltages of the diodes D66, D67 must be set higher than the absolute value of the high-voltage signal that is applied. In other words, in the diodes D66, D67, the breakdown voltages are set in such a manner that even if high voltages of this kind are applied in respectively opposite directions, avalanche breakdown does not occur and current does not flow in opposite directions in the diodes.

Figure 7:
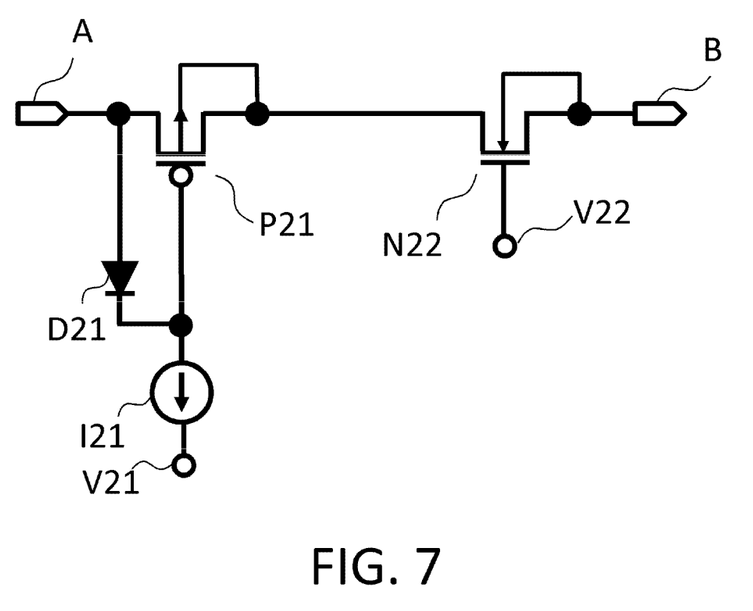
FIG. 7 is a diagram showing a further example of a protection circuit according to the first embodiment.

FIG. 7 is a diagram showing a further example of a protection circuit in the first embodiment, and constituent elements which are the same as FIG. 1 are labelled with the same reference numerals and description thereof is omitted apart from particular circumstances. In other words, the protection circuit shown in FIG. 7 adopts a circuit configuration in which back gates of the transistor P21 and the transistor N22 are connected to the respective sources. By adopting a configuration of this kind, it is possible to achieve an operation similar to that of the circuit in FIG. 2A, in accordance with the applied voltage and the voltage resistance of the device. Furthermore, by connecting the back gates of the transistor P21 and the transistor N22 to the respective sources, it is possible to operate the transistors in a stable fashion.

Second Embodiment

Figure 8A:
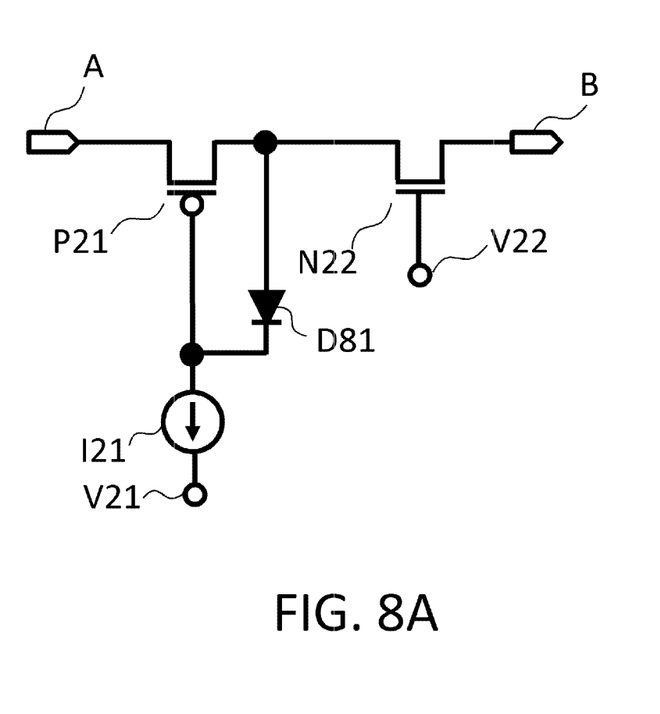
FIGS. 8A and 8B are diagrams showing the configuration of a second embodiment of a protection circuit in an ultrasound diagnostic apparatus according to the present invention.
Figure 8B:
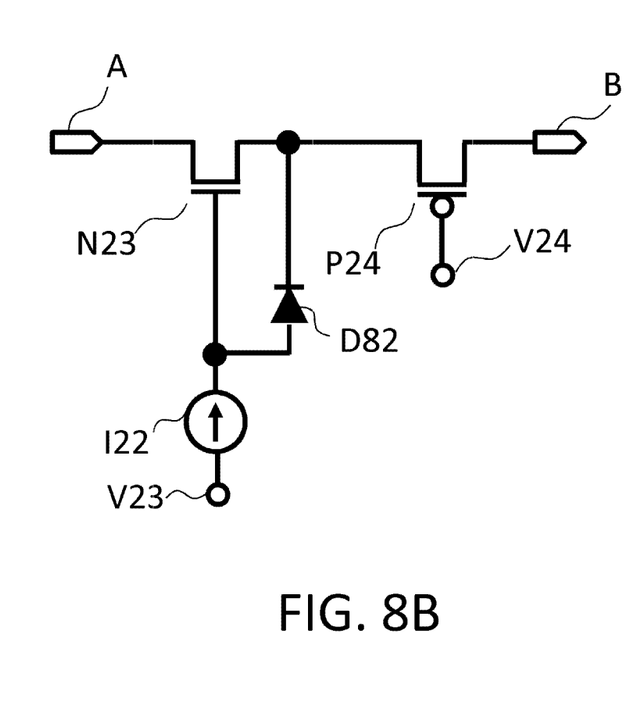

FIG. 8A and FIG. 8B are diagrams showing a second embodiment of a protection circuit in the ultrasound diagnostic apparatus according to the present invention, and constituent elements which are the same as FIG. 1 are labelled with the same reference numerals and description thereof is omitted apart from particular circumstances. The protection circuit of the present embodiment is configured such that the gate protection diodes D21, D22 in the protection circuits illustrated in FIGS. 2A and 2B of the first embodiment are connected to the sources of the transistors P21, N23, as in the diodes D81, D82 illustrated in FIGS. 8A and 8B. In this way, similarly to the first embodiment, the gate-source voltage of the transistors P21, N22 illustrated in FIGS. 8A and 8B is limited so as to become the threshold voltage of the diode D81, D82 (forward-direction voltage fall). By adopting this configuration, it is possible to prevent gate breakdown in the transistors P21 and N22. In the case of this configuration, since the protection diode D81 is located between the gate and source of the transistor P21 illustrated in FIG. 8A, for example, then it is possible to limit the gate-source voltage to the threshold value of the diode D81, at most. Furthermore, in the case of the circuit configuration illustrated in FIG. 8A, a high voltage is not applied to both ends of the diode D81, compared to the protection circuit illustrated in FIG. 2A, for example, of the first embodiment. This is because the anode of the diode D81 is not connected directly to the terminal A to which the high-voltage signal is applied, but is connected to the source of the transistor P21. Therefore, it is possible to design the diode with a low voltage resistance compared to that required in the protection diode in FIG. 2A. In FIG. 8B, the circuit configuration is the same as FIG. 8A apart from the fact that the polarities are opposite.

Third Embodiment

Figure 9A:
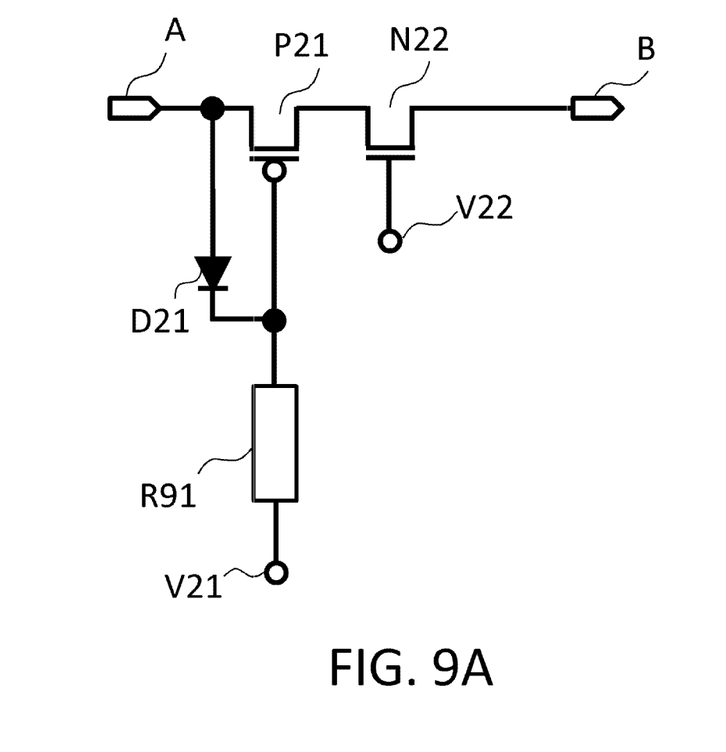
FIGS. 9A and 9B are diagrams showing the configuration of a third embodiment of a protection circuit in an ultrasound diagnostic apparatus according to the present invention.
Figure 9B:
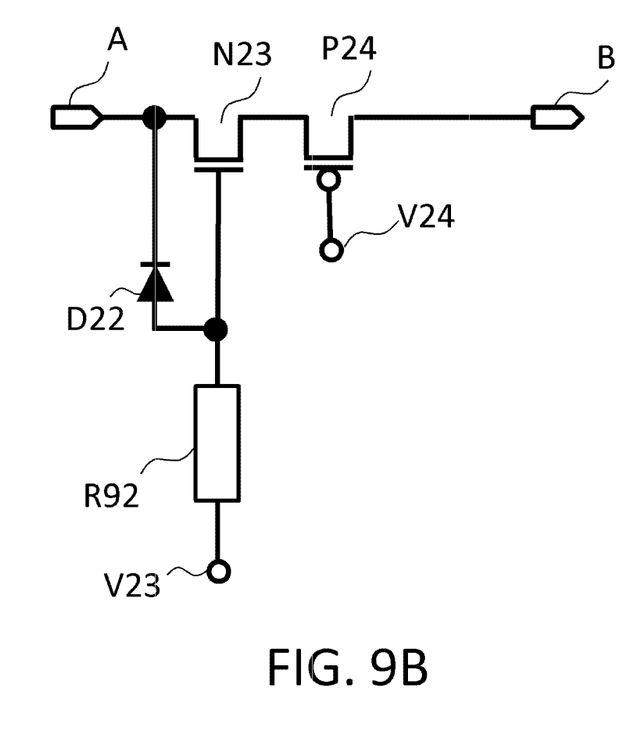

FIG. 9A and FIG. 9B are diagrams showing a third embodiment of a protection circuit in the ultrasound diagnostic apparatus according to the present invention, and constituent elements which are the same as FIG. 1 are labelled with the same reference numerals and description thereof is omitted apart from particular circumstances. The protection circuit illustrated in FIGS. 9A and 9B of the present embodiment has a configuration in which the current sources I21, I22 of the protection circuit illustrated in FIG. 2A and FIG. 2B of the first embodiment are replaced with resistances R91 and R92.

The operation of the protection circuits illustrated in FIG. 9A and FIG. 9B is now described. The protection circuits illustrated in FIG. 9A and FIG. 9B have mutually reverse polarities but have the same basic function apart from this, and therefore the description is given here in relation to FIG. 9A only. When a low-voltage signal is applied to the terminal A, if the gate-source resistance and the gate-drain resistance of the transistor P21 are sufficiently larger than the resistance R91, then substantially no current flows in the resistance R91, and therefore substantially the same voltage as the constant voltage V21 is present at the gate of the transistor P21. Therefore, the transistor P21 switches on. On the other hand, when the high-voltage signal is applied to the terminal A, the current flowing in the diode D21 is limited by the resistance value of the resistance R91. Furthermore, since a protection circuit can be achieved by one resistance, as opposed to achieving a protection circuit by a current source, then it is possible to reduce the size of the circuit and also to design the circuit at low cost.

Further Embodiments

All diodes in the first, second and third embodiments can employ any element that has a function of limiting the voltage to a particular voltage and passing current. For example, a MOS transistor or a bipolar transistor in a diode connection, or the like, may be used. Furthermore, these diodes may be configured in a multiple serial connection. Moreover, similar functions to the diodes D21, D22 illustrated in FIGS. 2A and 2B and the diodes D81, D82 illustrated in FIGS. 8A and 8B can be achieved by resistances.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2014-234525, filed on Nov. 19, 2014, which is hereby incorporated by reference herein in its entirety.

What is claimed is:
1. A protection circuit comprising:
 a first enhancement-type MOS transistor of a first conductivity type having a drain, a source, and a gate;
 a second enhancement-type MOS transistor of a second conductivity type having a drain connected to the source of the first enhancement-type MOS transistor, a source, and a gate to which a first bias voltage is supplied;

a diode element having one end connected to the drain of the first enhancement-type MOS transistor, and another end connected to the gate of the first enhancement-type MOS transistor; and a current source having one end connected to the gate of the first enhancement-type MOS transistor and the other end of the diode element, and another end to which a second bias voltage is supplied, wherein a forward-direction threshold voltage of the diode element is greater than a threshold voltage of the first enhancement-type MOS transistor, wherein the first enhancement-type MOS transistor switches off on the basis of the voltage present at the source thereof, when a first voltage signal of a first polarity having an absolute value greater than a prescribed value is applied to the drain of the first enhancement-type MOS transistor, wherein the second enhancement-type MOS transistor switches off on the basis of the voltage present at the source thereof, when a first voltage signal of a second polarity having an absolute value greater than a prescribed value is applied to the drain of the first enhancement-type MOS transistor, and wherein the first and second enhancement-type MOS transistors switch on when a second voltage signal having an absolute value smaller than a prescribed value and smaller than the absolute value of the first voltage signal is applied to the drain of the first enhancement-type MOS transistor.

2. The protection circuit according to claim 1, wherein the diode element is a parasitic diode of the first enhancement-type MOS transistor.

3. The protection circuit according to claim 1, wherein, when a first voltage signal of a first polarity having an absolute value greater than a prescribed value is applied to the drain of the first enhancement-type MOS transistor, the second bias voltage is supplied from the current source to the gate of the first enhancement-type MOS transistor and the first enhancement-type MOS transistor switches off on the basis of the prescribed second bias voltage.

4. The protection circuit according to claim 1, wherein the first and second polarities are respectively negative and positive, wherein the first enhancement-type MOS transistor is an enhancement-type P-channel MOS transistor, wherein the second enhancement-type MOS transistor is an enhancement-type N-channel MOS transistor, wherein the second bias voltage is greater than the sum of the negative first voltage signal and a threshold voltage of the enhancement-type P-channel MOS transistor, and wherein the first bias voltage is smaller than the sum of the positive first voltage signal and a threshold voltage of the enhancement-type N-channel MOS transistor.

5. The protection circuit according to claim 1, wherein the first and second polarities are respectively positive and negative, wherein the first enhancement-type MOS transistor is an enhancement-type N-channel MOS transistor, wherein the second enhancement-type MOS transistor is an enhancement-type P-channel MOS transistor, wherein the second bias voltage is smaller than the sum of the positive first voltage signal and a threshold voltage of the enhancement-type N-channel MOS transistor, and wherein the first bias voltage is greater than the sum of the negative first voltage signal and a threshold voltage of the enhancement-type P-channel MOS transistor.

6. The protection circuit according to claim 1, further comprising a voltage limiting circuit which limits the absolute value of the voltage signal present at the source of the second enhancement-type MOS transistor to no higher than voltage resistance of an external circuit which is connected to the source of the second enhancement-type MOS transistor.

7. The protection circuit according to claim 6, wherein the voltage limiting circuit is a clip circuit or a clamp circuit.

8. The protection circuit according to claim 1, wherein a back gate and the source of the first enhancement-type MOS transistor are connected, and wherein a back gate and the source of the second enhancement-type MOS transistor are connected.

9. A protection circuit comprising:

a first enhancement-type MOS transistor of a first conductivity type having a drain, a source, and a gate;

a second enhancement-type MOS transistor of a second conductivity type having a drain connected to the source of the first enhancement-type MOS transistor, a source, and a gate to which a first bias voltage is supplied;

a diode element having one end connected to the source of the first enhancement-type MOS transistor, and another end connected to the gate of the first enhancement-type MOS transistor; and a current source having one end connected to the gate of the first enhancement-type MOS transistor and the other end of the diode element, and another end to which a second bias voltage is supplied, wherein a forward-direction threshold voltage of the diode element is greater than a threshold voltage of the first enhancement-type MOS transistor, wherein the first enhancement-type MOS transistor switches off on the basis of the voltage present at the source thereof, when a first voltage signal of a first polarity having an absolute value greater than a prescribed value is applied to the drain of the first enhancement-type MOS transistor, wherein the second enhancement-type MOS transistor switches off on the basis of the voltage present at the source thereof, when a first voltage signal of a second polarity having an absolute value greater than a prescribed value is applied to the drain of the first enhancement-type MOS transistor, and wherein the first and second enhancement-type MOS transistors switch on when a second voltage signal having an absolute value smaller than a prescribed value and smaller than the absolute value of the first voltage signal is applied to the drain of the first enhancement-type MOS transistor.

10. A protection circuit comprising:

a first enhancement-type MOS transistor of a first conductivity type having a drain, a source, and a gate;

a second enhancement-type MOS transistor of a second conductivity type having a drain connected to the source of the first enhancement-type MOS transistor, a source, and a gate to which a first bias voltage is supplied;

a diode element having one end connected to the drain of the first enhancement-type MOS transistor, and another end connected to the gate of the first enhancement-type MOS transistor; and a resistance having one end connected to the gate of the first enhancement-type MOS transistor and the other end of the diode element, and another end to which a second bias voltage is supplied, wherein a forward-direction threshold voltage of the diode element is greater than a threshold voltage of the first enhancement-type MOS transistor, wherein the first enhancement-type MOS transistor switches off on the basis of the voltage present at the source thereof, when a first voltage signal of a first polarity having an absolute value greater than a prescribed value is applied to the drain of the first enhancement-type MOS transistor, wherein the second enhancement-type MOS transistor switches off on the basis of the voltage present at the source thereof, when a first voltage signal of a second polarity having an absolute value greater than a prescribed value is applied to the drain of the first enhancement-type MOS transistor, and wherein the first and second enhancement-type MOS transistors switch on when a second voltage signal having an absolute value smaller than a prescribed value and smaller than the absolute value of the first voltage signal is applied to the drain of the first enhancement-type MOS transistor.

11. The protection circuit according to claim 1, wherein the first voltage signal exceeds voltage resistance of the external circuit, and wherein the second voltage signal does not exceed voltage resistance of the external circuit.

12. The protection circuit according to claim 11, wherein the first voltage signal is a signal used when an ultrasound transducer of an ultrasound diagnostic apparatus transmits an ultrasound wave to an object, wherein the second voltage signal is a signal output due to the ultrasound transducer receiving an acoustic wave reflected from the object, on the basis of the transmission of the ultrasound wave, and wherein the external circuit is an amplification circuit which amplifies the second voltage signal.

13. A transmission and reception circuit comprising:

the protection circuit according to claim 1;

an amplification circuit; and a transmission circuit, wherein the amplification circuit is connected to an output end of the protection circuit and amplifies a voltage signal having an absolute value that is smaller than a prescribed value and that is output from the protection circuit, and wherein the transmission circuit is connected to an input end of the protection circuit and transmits a voltage signal having an absolute value that is greater than a prescribed value.

14. An ultrasound diagnostic apparatus comprising:

the transmission and reception circuit according to claim 13; and an transducer, wherein the transducer transmits an ultrasound wave on the basis of a voltage signal transmitted from the transmission circuit and outputs a voltage signal upon receiving the ultrasound wave.

\* \* \* \* \*